(12) United States Patent
Rao et al.

(10) Patent No.: US 10,206,904 B2
(45) Date of Patent: Feb. 19, 2019

(54) LICOFELONE DERIVATIVES AND METHODS OF USE

(71) Applicant: The Board of Regents of the University of Oklahoma, Norman, OK (US)

(72) Inventors: Chinthalapally V. Rao, Oklahoma City, OK (US); Naveena B. Janakiram, Poolesville, MD (US); Hariprasad Gali, Edmond, OK (US); Altaf Mohammed, Edmond, OK (US); Gopal Pathuri, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 15/745,603

(22) PCT Filed: Jul. 13, 2016

(86) PCT No.: PCT/US2016/042009
§ 371 (c)(1),
(2) Date: Jan. 17, 2018

(87) PCT Pub. No.: WO2017/015013
PCT Pub. Date: Jan. 26, 2017

(65) Prior Publication Data
US 2018/0207129 A1    Jul. 26, 2018

Related U.S. Application Data

(60) Provisional application No. 62/194,071, filed on Jul. 17, 2015.

(51) Int. Cl.
| | |
|---|---|
| *A61K 31/407* | (2006.01) |
| *A61K 31/403* | (2006.01) |
| *A61P 29/00* | (2006.01) |
| *A61P 35/00* | (2006.01) |
| *C07D 209/52* | (2006.01) |

(52) U.S. Cl.
CPC .......... *A61K 31/407* (2013.01); *A61K 31/403* (2013.01); *A61P 29/00* (2018.01); *A61P 35/00* (2018.01); *C07D 209/52* (2013.01)

(58) Field of Classification Search
CPC .......................... C07D 209/52; C07D 209/00
See application file for complete search history.

(56) References Cited

U.S. PATENT DOCUMENTS

| | | | | |
|---|---|---|---|---|
| 5,942,535 | A * | 8/1999 | Laufer ................ | C07D 513/04 514/256 |
| 6,417,371 | B1 | 7/2002 | Kammermeier et al. | |
| 8,519,155 | B2 | 8/2013 | Albrecht et al. | |
| 8,945,626 | B2 | 2/2015 | Elphick et al. | |
| 2010/0234452 | A1* | 9/2010 | Mian ................... | A61K 31/166 514/440 |
| 2015/0306232 | A1* | 10/2015 | Xu ....................... | A61K 9/0014 514/569 |

FOREIGN PATENT DOCUMENTS

| | | | |
|---|---|---|---|
| WO | 2007072503 A3 | 6/2007 | |
| WO | 2008012110 A2 | 1/2008 | |
| WO | 2009056077 A3 | 5/2009 | |
| WO | WO-2009056077 A2 * | 5/2009 | ........... C07D 487/04 |

OTHER PUBLICATIONS

S. Rádl et al., 49 Tetrahedron Letters, 5316-5318 (2008).*
IN0008-DEL-2004; Abstract from Indian Patent Application; published Feb. 10, 2006; 25 pages.
Biava, M., et al.; "Enhancing the pharmacodynamic profile of a class of selective COX-2 inhibiting nitric oxide donors"; Bioorganic & Medicinal Chemistry; 22 (2014) 772-786.
PCT/US2016/042009; International Search Report and Written Opinion; dated Sep. 27, 2016; 13 pages.

* cited by examiner

Primary Examiner — Alexander R Pagano
(74) Attorney, Agent, or Firm — Hall Estill Law Firm

(57) ABSTRACT

Derivatives of licofelone for the treatment of chronic inflammatory diseases and epithelial cancers associated with chronic inflammation are disclosed. The agents target mPGES-1 and 5-LOX.

9 Claims, 9 Drawing Sheets

LICOFELONE DERIVATIVES AND METHODS OF USE

CROSS-REFERENCE TO RELATED APPLICATIONS

The present application is a national stage application of a PCT application having International Application No. PCT/US2016/042009, filed Jul. 13, 2016, which claims priority to U.S. Provisional Application having U.S. Ser. No. 62/194,071, filed Jul. 17, 2015, which claims the benefit under 35 U.S.C. 119(e), the disclosure of which is hereby expressly incorporated herein by reference.

BACKGROUND

Epidemiological, preclinical and clinical data suggests that inflammation plays a key role in colon-rectal cancer (CRC). Studies suggest that CRC risk is high in subjects with ulcerative colitis (UC) and Crohn disease (CD). Globally, CRC is the third most commonly diagnosed cancer and second leading cause of deaths in United States. It is estimated that there will be 1.35 million new cases and about 700,000 deaths worldwide at annual bases; and 142,820 new cases diagnosed in the United States in 2013 and 50,830 deaths due to this disease. It is widely reported and accepted that inflammatory genes, such as cyclooxygenase-2 (COX-2) expression, and its metabolite prostaglandin-$E_2$ ($PGE_2$) play key roles in CRC progression and metastasis. There are multiple levels of control exits for regulation of $PGE_2$ production. Use of anti-inflammatory agents displayed protective effects in CRC, which stimulated interest in primary prevention with use of agents belonging to nonsteroidal antiinflammatory drugs (NSAIDs) and selective COX-2 inhibitors. Compelling protective effects were shown by NSAIDs like aspirin and selective COX-2 inhibitors in animal models and clinical research. Though NSAIDs were effective in showing preventive effects of CRC, they are associated with gastrointestinal bleeding due to inhibition of cyclooxygenase-1 (COX-1) along with cyclooxygenase-2 (COX-2). A large number of clinical studies with varying designs followed with similar results with NSAIDs and selective COX-2 inhibitors. Selective COX-2 inhibitors provided better efficacy and to a certain extent were devoid of gastrointestinal toxicities. There have been several placebo-controlled trials on the use of COX-2 inhibitors in the prevention of adenoma recurrence in Familial Adenomatous polyposis (FAP), an inherited disorder characterized by colon and rectal cancer, and sporadic patients with a prior history of adenoma. One of the trials with selective COX-2 inhibitor provided 30-55% lower risk of adenoma recurrence it was associated with higher risk of cardiovascular (CV) events. Therefore, the cancer-protective benefits of selective COX-2 inhibitors appear to be outweighed by an increase in risk of cardiovascular events, due to platelet dependent thrombosis. The reason for this toxicity appears to be due to imbalance of COX and lipoxygenase (LOX) enzymes due to inhibition of COX-2 leading blocking $PGE_2$ but also prostaglandin-$E_2$ ($PGI_2$); moreover, shifting metabolism LOX metabolites such leukotrienes (LTs). Both low levels of $PGI_2$ and high levels of LTs are established risk factors of thrombosis and CV risk.

5-LOX and its downstream molecule leukotriene $B_4$ ($LTB_4$) are identified to be involved in CRC development. Similar to COX-2 and its downstream $PGE_2$, 5-LOX and $LTB_4$ are highly elevated in CRC, related to tumor size and invasion. Thus, blocking of $PGE_2$ and LTs by sparing the $PGI_2$ is a significant issue in developing anticancer agents without unwanted side effects and CV risk. Mechanistically, one such control is via expression of specific prostaglandin E synthases, which utilize the COX product prostaglandin-$H_2$ $PGH_2$ to produce $PGE_2$. Microsomal prostaglandin E synthase-1 (mPGES-1) is, like COX-2, induced by pro-inflammatory stimuli and up-regulated in colorectal tumors and major contributor of $PGE_2$. In support of this hypothesis, loss of mPGES-1 expression is reported to suppress intestinal neoplasia in Apc-mutant mice. Thus, selectively targeting mPGES-1 would block the production of $PGE_2$ but spare the $PGI_2$ which is required for the anti-thrombotic effects in avoiding cardiovascular (CV) risk. COX-1 and COX-2 are responsible for production of PG's, thus inhibiting can reduce pain and inflammation, however, this inhibition can also cause alternative processing of arachidonic acid via 5-LOX pathway resulting in an increase of proinflammatory and gastrotoxic LT's.

Molecular mechanistic studies suggest that targeting mPGES-1 and 5-LOX would spare the $PGI_2$ and cardiovascular and renal side effects. Licofelone (2,2-dimethyl-6-(4-chloropheny-7-phenyl-2,3-dihydro-1H-pyrrazoline-5-yl] acetic acid), discovered by Merckle GmbH and developed by EuroAlliance, is a competitive 5-LOX, COX-1 and COX-3 inhibitor. It decreases the production of both LTs and PGs, thereby reducing inflammation and pain with low gastrotoxicity. It thus possesses significant analgesic, anti-inflammatory, and antiasthmatic effects at doses that cause no gastrointestinal (GI) side effects. Thus, designing and development of anti-inflammatory drugs which are devoid of GI toxicity, and prothrombotic and nephro-toxicities are a significant clinical need for many diseases including CRC prevention and treatment.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein.

DETAILED DESCRIPTION

Figure 1:
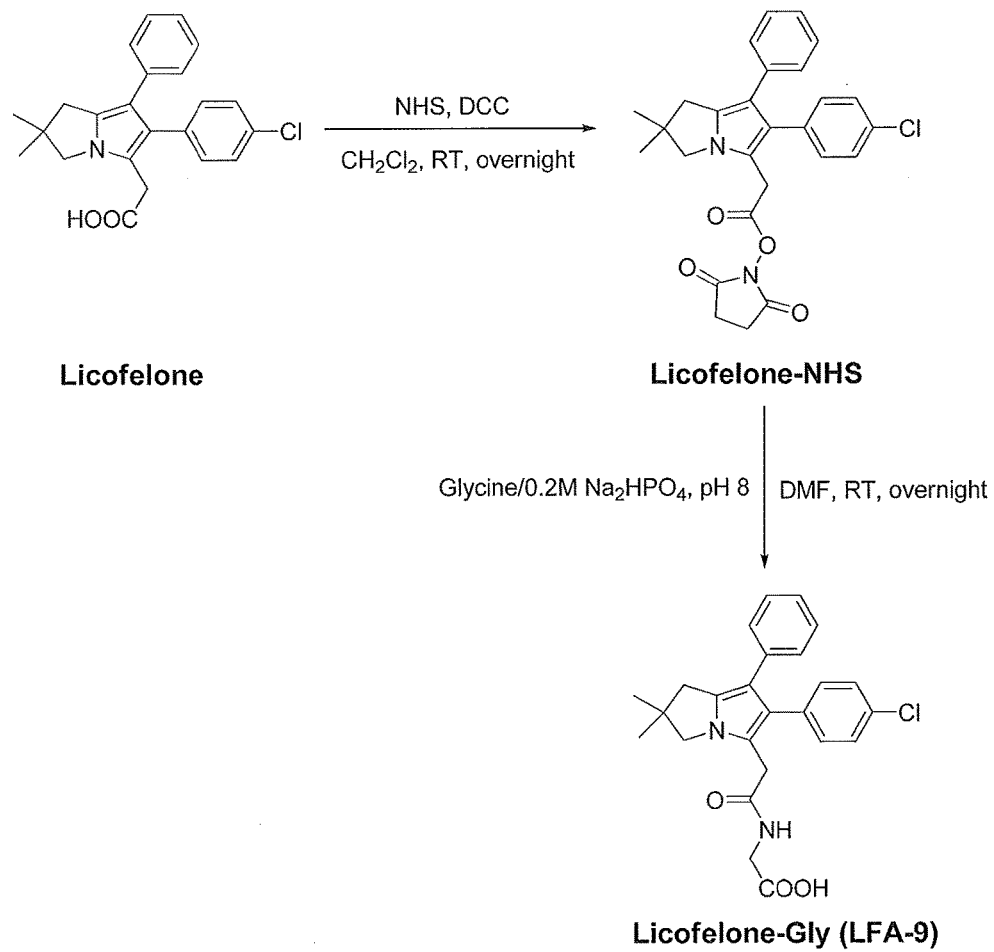
FIG. 1 is a schematic of the synthesis of licofelone-glycine (LFA-9) from licofelone.

New anti-inflammatory drugs without unwanted side effects are needed for treatment of chronic inflammatory diseases, and epithelial cancers, such as epithelial cancers that are associated with chronic inflammation. In the present work, a number of agents which target mPGES-1 and 5-LOX, with limited renal uptake, were designed. Among the several agents synthesized, licofelone-glycine (LFA-9) is an analog of licofelone (a dual COX-LOX inhibitor), which showed high selectivity for mPGES-1 and 5-LOX inhibition. Based on initial experiments, we further investigated LFA-9 effects in rodent models for inflammation and tumorigenesis. We investigated the ability of LFA-9 to prevent the GI inflammation, ulceration and small intestinal (SI) and colon tumors inhibition in $Apc^{Min/+}$ mice and azoxymethane (AOM)-induced colon cancer, as explained in further detail below. LFA-9 and similar derivatives of licofelone provide prevention and treatment of epithelial cancers and chronic inflammatory diseases. Without wishing to be bound by theory it is believed that the licofelone derivatives disclosed herein act against such cancers and inflammatory diseases by (1) selectively targeting and inhibiting both mPGES-1 and 5-LOX, (2) inhibiting both in LPS/IL1b-induced RAW macrophages, and (3) significantly suppressing colonic tumor mPGES-1 and 5-LOX activity in a dose-dependent manner.

Before further describing various embodiments of the compositions and methods of the present disclosure in more detail by way of exemplary description, examples, and results, it is to be understood that the embodiments of the present disclosure are not limited in application to the details of methods and compositions as set forth in the following description. The description provided herein is intended for purposes of illustration only and is not intended to be construed in a limiting sense. The inventive concepts of the present disclosure are capable of other embodiments or of being practiced or carried out in various ways. As such, the language used herein is intended to be given the broadest possible scope and meaning; and the embodiments are meant to be exemplary, not exhaustive, and it is not intended that the present disclosure be limited to these particular embodiments. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compositions and methods of production and application and use thereof disclosed herein can be made and executed without undue experimentation in light of the present disclosure. Thus, while the compositions and methods of the present disclosure have been described in terms of particular embodiments, it will be apparent to those of skill in the art that variations may be applied to the formulations, compounds, or compositions and/or methods and in the steps or in the sequence of steps of the method described herein without departing from the spirit and scope of the inventive concepts of the present disclosure.

All patents, published patent applications, and non-patent publications mentioned in the specification are indicative of the level of skill of those skilled in the art to which the present disclosure pertains. Further, all patents, published patent applications, and non-patent publications referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal, and more particularly, humans. Animals which fall within the scope of the term "subject" as used herein include, but are not limited to, dogs, cats, rats, mice, guinea pigs, chinchillas, horses, goats, ruminants such as cattle, sheep, swine, poultry such as chickens, geese, ducks, and turkeys, zoo animals, Old and New World monkeys, and non-human primates.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent (licofelone derivative) which is sufficient to exhibit a detectable therapeutic effect without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

In certain non-limiting embodiments, the dosage of the licofelone derivative administered to a subject could be in a range of 1 µg per kg of subject body mass to 500 mg/kg, or in a range of 100 µg per kg to 250 mg/kg, or in a range of 1 mg per kg to 100 mg/kg, or in a range of 10 mg compound per kg to 100 mg/kg, or in a range of 25 mg per kg to 75 mg/kg.

The dosage(s) can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting example of a therapeutic method of the presently disclosed inventive concepts, the composition is provided in an IV infusion. Administration of the compounds used in the pharmaceutical composition or to practice the method of the presently disclosed inventive concepts can be carried out in a variety of conventional ways, such as, but not limited to, orally, by inhalation, rectally, or by cutaneous, subcutaneous, intraperitoneal, vaginal, or intravenous injection. Oral formulations may be formulated such that the compounds pass through a portion of the digestive system before being released, for example it may not be released until reaching the small intestine, or the colon.

When a therapeutically effective amount of the composition is administered orally, it may be in the form of a solid or liquid preparations such as capsules, pills, tablets, lozenges, melts, powders, suspensions, solutions, elixirs or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition may contain a solid carrier, such as a gelatin or an adjuvant. The tablet, capsule, and powder may contain from about 0.05 to about 95% of the active substance compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition particularly contains from about 0.005 to about 95% by weight of the active substance. For example, a dose of about 10 mg to about 1000 mg once or twice a day could be administered orally.

In another embodiment, the compositions of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the compositions in an aqueous or non-aqueous pharmaceutically acceptable solvent which may also contain suspending agents, sweetening agents, flavoring agents, and preservative agents as are known in the art.

For parenteral administration, for example, the compositions may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives and buffers as are known in the art.

When an effective amount of the compound or composition is administered by intravenous, cutaneous, or subcutaneous injection, the compound is particularly in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the active agent(s), an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition(s) of the present disclosure may also contain stabilizers, preservatives, buffers, antioxidants, or other additives known to those of skill in the art.

As noted, particular amounts and modes of administration can be determined by one skilled in the art. One skilled in the art of preparing formulations can readily select the proper form and mode of administration, depending upon the particular characteristics of the compositions selected, the infection to be treated, the stage of the infection, and other relevant circumstances using formulation technology known in the art, described, for example, in *Remington: The Science and Practice of Pharmacy*, 21$^{st}$ ed.

Additional pharmaceutical methods may be employed to control the duration of action of the compositions. Increased half-life and/or controlled release preparations may be achieved through the use of polymers to conjugate, complex with, and/or absorb the active substances described herein. The controlled delivery and/or increased half-life may be achieved by selecting appropriate macromolecules (for example but not by way of limitation, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release. The compounds may also be ionically or covalently conjugated to the macromolecules described above.

Another possible method useful in controlling the duration of action of the compounds or compositions by controlled release preparations and half-life is incorporation of the compounds into particles of a polymeric material such as polyesters, polyamides, polyamino acids, hydrogels, poly (lactic acid), ethylene vinylacetate copolymers, copolymer micelles of, for example, polyethylene glycol (PEG) and poly(1-aspartamide).

Non-limiting examples of acetoamido derivatives of licofelone of the present disclosure are represented by the following structure (Structure 1):

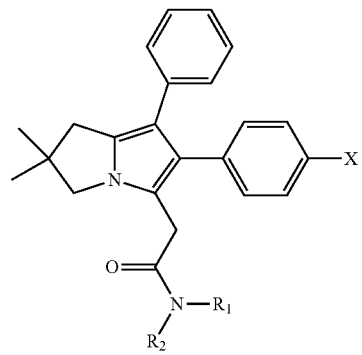

wherein X is selected from the group consisting of F, Cl, Br, and I; and each of $R_1$ and $R_2$ may be, but is not limited to, H; $CH_2(CH_2)_n OH$, where n=1-3, e.g., $CH_2CH_2OH$; $CH_2(CH_2)_m COOH$, where m=0-3, e.g., $CH_2COOH$ and $CH_2CH_2COOH$; $CH((CH_2)_m CH_3)COOH$, where m=0-3, e.g., $CH(CH_3)COOH$; $CH((CH_2)_n OH)COOH$, where n=1-3, e.g., $CH(CH_2OH)COOH$; $CH((CH_2)_n COOH)COOH$, where n=1-3, e.g., $CH(CH_2COOH)COOH$ and $CH(CH_2CH_2COOH)COOH$; $CH_2(CH_2)_n NH_2$, where n=1-3, e.g., $CH_2CH_2NH_2$; $CH((CH_2)_n CONH_2)COOH$, where n=1-3, e.g., $CH(CH_2CONH_2)COOH$ and $CH(CH_2CH_2CONH_2)COOH$; $CH((CH_2)_n NH_2)COOH$, where n=1-3, e.g., $CH(CH_2NH_2)COOH$ and $CH(CH_2CH_2CH_2NH_2)COOH$; $CH((CH_2)_n NHC(NH)NH_2)COOH$, where n=1-3, e.g., $CH(CH_2CH_2CH_2NHC(NH)NH_2)COOH$; or $CH_2(CH_2)_n F$, where n=1-3, e.g., $CH_2CH_2F$; and with the proviso that no more than one of $R_1$ and $R_2$ is H. In one non-limiting embodiment of the compound, known as licofelone-glycine (LFA-9), X=Cl, $R_1$=H and $R_2$=$CH_2COOH$, or $R_2$=H and $R_1$=$CH_2COOH$.

Examples of diseases and conditions which can be treated with the compounds of the present disclosure include, but are not limited to, chronic inflammatory diseases, or diseases which have a chronic inflammatory component, such as but not limited to, atherosclerosis, diabetes, inflammatory bowel diseases, arthritis, psoriasis, autoimmune diseases, and Alzheimer's disease. Examples of diseases and conditions which can be treated with the compounds of the present disclosure also include cancers which are associated with a chronic inflammatory component, such as but not limited to, epithelial carcinoma cancers such as colorectal, pancreatic, lung, peritoneal, bladder, breast, prostate, renal, liver, bile duct, testicular, skin, stomach, ovarian, fallopian tube, and uterine cancers.

Examples

The present disclosure will now be discussed in terms of several specific, non-limiting, examples. The examples described below, which include particular embodiments, will serve to illustrate the practice of the present disclosure, it being understood that the particulars shown are by way of example and for purposes of illustrative discussion of particular embodiments and are presented in the cause of providing what is believed to be a useful and readily understood description of procedures as well as of the principles and conceptual aspects of the present disclosure.

Synthesis of Licofelone-Glycine (LFA-9)

The synthesis of LFA-9 was achieved in a two-step synthetic strategy (FIG. 1). First, to a solution of licofelone (28.45 g, 75 mmol) in dichloromethane ($CH_2Cl_2$) (300 mL) was added N-hydroxysuccinimide (NHS) (9.50 g, 82.5 mmol) in dichloromethane (300 mL) and N,N'-dicyclohexylcarbodiimide (DCC) (17.03 g, 82.5 mmol) in dichloromethane (100 mL). The reaction mixture was stirred at room temperature (RT) for overnight. The progress of the reaction was monitored by TLC. After completion of reaction, N,N'-dicyclohexylurea (a byproduct) was filtered on a sintered funnel and filtrate was evaporated on a rotary evaporator under reduced pressure to obtain licofelone-NHS in a quantitative yield. This compound was used immediately for the next step without further purification. Second, to a solution of licofelone-NHS (35.79 g, 75 mmol) in N,N-dimethylformamide (DMF) (650 mL) was added glycine (5.63 g, 75 mmol) in 0.2M $Na_2HPO_4$ (100 mL, pH 8.0). The reaction mixture was stirred at room temperature for overnight. The progress of the reaction was monitored by TLC. After completion of reaction, solvents were evaporated on a rotary evaporator under reduced pressure, and the product was extracted into ethyl acetate (2×300 mL). The combined organic layer was washed with water (2×100 mL) and with brine (2×100 mL). The organic layer was dried over sodium sulfate and solvents were evaporated on a rotary evaporator under reduced pressure to obtain the crude LFA-9. The crude compound was purified on a silica gel column by eluting with ethyl acetate to obtain the pure LFA-9 as a white solid (16.50 g, 50.3%). Alternatively, the crude compound was purified by recrystallization using ethyl acetate/hexane solvent mixture (26.40 g, 80.51%). (Melting Point: 106-108° C., $^1$H NMR (300 MHz, $CDCl_3$) δ (ppm): 1.29 (s, 6H, 2×$CH_3$), 2.85 (s, 2H, $CH_2$), 3.55 (s, 2H, $CH_2$), 3.72 (s, 2H, $CH_2$), 4.04 (d, $J_{gem}$=5.3 Hz, 2H, NH—$CH_2$), 7.03-7.29 (m, 9H, Ar—H). $^{13}$C NMR (75 MHz, $CDCl_3$) δ (ppm): 28.0, 33.0, 40.6, 41.2, 43.3, 58.0, 115.0, 117.2, 124.3, 124.8, 2×128.0, 128.5, 131.2, 131.9, 134.1, 134.9, 135.5, 171.4, 172.9. ESI-MS: m/z 435[M-H]$^-$).

Animal Studies

Animals:

Pathogen-free inbred male Fischer (F344) rats were obtained from Harlan Laboratories in required quantities. A series of tests to verify the health of the animals was performed, and the animals were transferred to the experimental room only when all tests certified their excellent health.

Experimental Diets/Preparation/Quality Control:

Adequate and controlled nutrition for laboratory animals is essential to achieve reproducibility of data. We used purified diets based on the American Institute of Nutrition (AIN)-76A modified diet (modifications with Dextrose and higher corn starch in place of sucrose (Casein, 20%; Corn Starch, 52%; Dextrose 13%, Corn oil, 5.0%; Alphacel/cellulose, 5.0%; DL-Methionine, 0.3%; Mineral mix AIN, 3.5%; Vitamin mix, AIN, 1.0%; and Choline bitartrate, 0.2%). All the experimental AIN-76A modified diets were formulated and prepared at the rodent barrier research diet formulation core lab. All ingredients of the purified diet were purchased in bulk from the Bioserv, N.J. All diets ingredients were mixed thoroughly so that all micronutrients are uniformly distributed. In order to assure that LFA-9 uniformly distributed in the diet, these agents were pre-mixed with a small quantity of control diet in a food mixer, added to pre-weighed amounts of control diet in a Hobart Mixer and mixed thoroughly for about 45 minutes. Then aliquots of samples taken from the top, middle and bottom portions of the diets were analyzed for agents homogeneity of the experimental diets. We have established frequency of preparation of experimental diets containing LFA-9, by measuring the stability of this agent in the diet each day for 7 days. LFA-9 stored in food cups for seven days showed >96% stability. Based on this information, frequency of preparation of experimental diets was once a week, and food cups were changed 3 times a week. All diets were stored in air-tight containers at 4° C. in a cold room.

I. Maximum Tolerated Dose (MTD) and GI Ulceration:

The MTD and the dosage levels of LFA-9 for inhibiting mPGES-1 and 5-LOX were investigated in the male C57B6/J mice model. LFA-9 was administered in the diet, 100 ppm to 1,600 ppm, respectively, dose range for 6 week period in mice. Body weights and symptoms of toxicity were recorded twice weekly for 6 weeks. We have compared LFA-9, with another mPGES-1 and 5-LOX select inhibitor (YS-121), as positive control for the potential activities. All organs were examined grossly for any abnormalities upon necropsy. Livers, kidney, stomach, intestinal tract, and blood were obtained from the animals and analyzed for Liver enzyme profile, GI ulceration, and levels of test agents.

GI Ulceration and Crypt toxicity:

Colonic ulceration grading was carried using following criteria.

Grade 0: No ulcerations or mucosal damage;
Grade 1: Up to 15 small mucosal ulcerations (<1 mm in diameter), observable only as slight depressions in reflected light;
Grade 2: Small mucosal ulcerations and ≤10 medium ulcerations (1-2 mm in diameter) with no ulcerations >2 mm in diameter;

were died at the end six-week exposure. In addition, we observed notable stomach ulceration (Grades 2 to 3) and colonic ulceration (Grade 1 to 2) at microscopic level in mice fed 1,600 ppm LFA-9; and an increase of serum liver enzyme levels were noticed. Gross pathology suggests that mice exposed to 1,600 ppm LFA-9 shows modest liver toxicity (Table 1). As shown in Table 1, YS-121 had significant toxicity at 75 ppm and above dose levels. Overall, bodyweight and gross histological observations suggest that 800 ppm LFA-9 administered in the diet do not induce any body weight loss or gross histological symptoms of toxicity in C57BL/6 mice.

TABLE 1

Effect of LFA-9 and YS-121 on gastrointestinal (GI) ulceration and liver enzymes levels (unit/L, Mean ± SEM) of male C57 mice.

| Experimental Groups | Dose (PPM) | Major Organ Toxicity | Ulceration (Grade) | | | Liver enzymes (units/L) | | | |
|---|---|---|---|---|---|---|---|---|---|
| | | | Stomach | Small Intestine | Colon | ALKP | LDH | AST | ALT |
| 1. Control | 0 ppm | None | Grade 0 | Grade 0 | Grade 0 | 165 ± 28 | 377 ± 35 | 64 ± 13 | 88 ± 12 |
| 2. LFA-9 | 100 ppm | None | Grade 0 | Grade 0 | Grade 0 | 178 ± 32 | 408 ± 28 | 75 ± 8.5 | 82 ± 15 |
| 3. LFA-9 | 200 ppm | None | Grade 0 | Grade 0 | Grade 0 | 184 ± 30 | 394 ± 19 | 83 ± 10 | 98 ± 13 |
| 4. LFA-9 | 400 ppm | None | Grade 0 | Grade 0 | Grade 0 | 187 ± 38 | 379 ± 29 | 68 ± 7.5 | 93 ± 15 |
| 5. LFA-9 | 800 ppm | None | Grade 0 | Grade 0 | Grade 0 | 181 ± 27 | 422 ± 43 | 82 ± 11 | 104 ± 13 |
| 6. LFA-9 | 1,600 | Liver | Grade 1 | Grade 0 | Grade 1 | 288 ± 24* | 589 ± 42* | 132 ± 17* | 158 ± 18* |
| 7. YS-121 | 25 ppm | None | Grade 0 | Grade 0 | Grade 0 | 183 ± 24 | 388 ± 29 | 77 ± 8.6 | 81 ± 11 |
| 8. YS-121 | 50 ppm | None | Grade 0 | Grade 0 | Grade 0 | 198 ± 33 | 451 ± 38 | 90 ± 7.8 | 96 ± 14 |
| 9. YS-121 | 75 ppm | Liver | Grade 1 | Grade 0 | Grade 0 | 358 ± 47* | 540 ± 51 | 118 ± 18* | 147 ± 17* |
| 10. YS-121 | 100 ppm | Liver* | Grade: 2-3 | Grade: 1 | Grade: 0, 1 | 477 ± 51* | 883 ± 68* | 169 ± 29* | 194 ± 23* |
| 11. YS-121 | 200 ppm | Liver** Stomach | Grade: 5 | Grade: 4 | Grade: 2 | — | — | — | — |

*Significantly different from the Control diet fed mice serum on liver enzyme levels Grade 3: Small and medium ulcerations ≤3 mm and <4 mm in diameter with no intestinal adhesions;
Grade 4: Predominantly medium and large ulcerations (>4 total) with large ulcerations exhibiting signs of perforations and adhesions which make it difficult to remove the intestine intact;
Grade 5: Necropsy of dead or euthanized animals reveals evidence of massive peritonitis resulting from intestinal perforations. All animals found dead will be necropsied to confirm that the most likely cause of death was due to intestinal ulcerations.

Results:

Rats administered with LFA-9 in the diet up to 800 ppm did not exhibit toxicity and gained bodyweights similar to control diet fed mice. However, dietary LFA-9 administration at 1,600 ppm lead to significant body weight retardation as compared to control diet fed mice. In mice fed 1,600 ppm LFA-9 for six weeks, we observed ~30% body weight loss (P<0.001) as compared to control diet fed mice body weight gain. Also, mice administered with 1,600 ppm LFA-9 showed the retardation of body weight growth and 3 animals II. Ex-Vivo Inhibitory Effect of LFA-9 on mPGES-1 and 5-LOX Using and $^{14}$C-AA, Respectively as Substrates:

Control diet fed AOM-induced rat colonic tumors were utilized to assess the inhibitory effect of LFA-9 on mPGES-1 and 5-LOX. We have utilized five different concentrations of LFA-9 to assess the enzyme inhibitory activities. Briefly, colonic tubular adenocarcinomas (ACs) were homogenized in 100 mM Tris-HCl buffer. Homogenized samples (100 mg protein) were incubated with reaction mixture containing 0 to 20 uM LFA-9 with $^{14}$C-PGH$_2$ (12 μmol=~500,000 CPM) for mPGES-1 assay or 0-20 uM along with $^{14}$C-AA (12 uM, ~600,000 CPM) for 5-LOX and COX-2 assays. Reaction mixture incubated for 20 min and $^{14}$C-PGE$_2$, 5-$^{14}$C-HETE and other 14-C metabolites were extracted and analyzed by Radio-HPLC according to the previously published work.

Results:

A dose dependent inhibition of mPGES-1 and 5-LOX was observed compared to control. An average concentration of 7.5 μM of LFA-9 inhibits the mPGES-1 and 5-LOX activities by ~57% and ~68%, respectively, with a minimum inhibition of COX-1/COX-2 (Table 2).

TABLE 2

Effect of LFA-9 and YS-121 on AOM-induced colonic tumor mPGES-1, 5-LOX and COX-2 enzymes levels by Ex-Vivo method; and effect on AOM/DSS-induced colonic mucosal AA metabolizing enzymes and inflammation in male F344 rats.

| Treatment | Concentration (µM) | % of Inhibition from control | | | Dose (PPM) | AOM-DSS-Induced | | | Inflammation Score |
|---|---|---|---|---|---|---|---|---|---|
| | | mPGES-1 * | 5LOX ** | COX-1/2 *** | | mPGES-1 | 5-LOX | COX-1/2 | |
| 1. Control | 0 | 0 | 0 | 0 | 0 | — | — | — | 2 to 3 |
| 2. LFA-9 | 2.5 | 18% | 27% | 4% | 100 | 22.6% | 14.5% | 3.8% | 1 |
| 3. LFA-9 | 5.0 | 32% | 49% | 9% | 200 | 33.7% | 22.6% | 8.9% | 0 to 1 |
| 4. LFA-9 | 7.5 | 57% | 68% | 22% | 400 | 58% | 63.7% | 15.7% | 0 |
| 5. LFA-9 | 10 | 78% | 89% | 31% | 600 | 77% | 74.7% | 31.3% | 0 |
| 6. LFA-9 | 20 | 83% | 97% | 58% | 800 | 83% | 88.3% | 42.6% | 0 |

\* Percentage of inhibition of $^{14}$C-PGE$_2$ from $^{14}$C-PGH$_2$ as compared to untreated colon tumor homogenates.
\*\* Percentage of inhibition of 5-$^{14}$C-HETE from $^{14}$C-AA as compared to untreated colon tumor homogenates.
\*\*\* Percentage of inhibition of $^{14}$C-PGs and TXs other from $^{14}$C-AA as compared to untreated colon tumor homogenates; ND, not determined.

III. Inhibition of AOM Plus DSS Induced Inflammation by LFA-9:

Male F344 rats at 8 weeks of age treated with AOM (15 mg/Kg BW) and exposed to 2% DSS for three days. Followed by this treatment rats were fed different dietary doses of LFA-9 (100-800 ppm) for two weeks, before the colonic mucosal samples were analyzed for mPGES-1, 5-LOX, and COX-2 activities. Results are summarized in Table 2 above. Further, the inflammation was scored by following below criteria:

Inflammation Score based on histological observations using the modified Sydney classification for colonic inflammation:

Following score criteria has been applied:
i. Score 0: No inflammation or changes in the colonic crypt morphology
ii. Score 1. Presence of neutrophil infiltration and chronic lymphocytic inflammation.
iii. Score 2. Surface epithelial damage, mild atrophy, lymphoid follicles
iv. Score 3: Severe atrophy and intestinal metaplasia.

Results:

Control diet fed rats treated with AOM/DSS showed predominately Score 2 inflammation, and fewer rats have inflammatory Score 3. All rats fed LFA-9 had inflammation Score 1 (lowest to highest doses) or no inflammation. Thus, LFA-9 at >100 ppm completely blocked inflammation.

IV. Effect of LFA-9 on AOM/DSS-Induced Colonic Aberrant Crypt Foci (ACF) Formation:

Table 3 summarizes the effect of LFA-9 on inhibiting colon ACF formation. ACF form before colorectal polyps and are an indicator of the potential for cancer. Both agents dose-dependently suppressed AOM-induced colonic ACF. Dietary LFA-9 at 600 ppm inhibited AOM-induced colonic total ACF and multi-crypt ACs by >60%.

Taken together, the above results indicate that LFA-9 up to 800 ppm level did not induce significant toxicity in male F344 rats. Accordingly the Rat AOM-induced colon tumor efficacy assays were run as 800 ppm as the highest dose.

TABLE 3

Determination of LFA-9 Dose-response effects of on DSS-induced colonic ACF in Male F344 rats.

| | Test Agent | # of Rats | Dose in diet (ppm) | Total ACF/Colon (Mean ± SEM) | % Inhibition | 4 or >multi-crypt AC/colon (Mean ± SEM) | % Inhibition |
|---|---|---|---|---|---|---|---|
| 1 | Control diet | 12 | 0 | 156 ± 7.8 | — | 33.5 ± 2.8 | — |
| 2 | LFA-9 | 12 | 200 | 110 ± 6.1 | 29.5% $P < 0.0001$ | 23.5 ± 2.1 | 30% $P < 0.008$ |
| 3 | LFA-9 | 12 | 400 | 84 ± 5.3 | 44.2% $P < 0.0001$ | 18.3 ± 2.0 | 45.4% $P < 0.0001$ |
| 4 | LFA-9 | 12 | 600 | 62 ± 4.8 | 60.5% $P < 0.0001$ | 13.5 ± 1.7 | 61.2% $P < 0.0001$ |

V. Determination of LFA-9 Induced Pharmacodynamic Tumor Efficacy Effects in Models of Colorectal Cancer.

(A) Efficacy of LFA-9 in Familial Adenomatous Polyposis (FAP) Model of Mice.

Breeding and Genotyping of Apc$^{Min/+}$ Mice:

All animal experiments were performed in accordance with the institutional guidelines of the American Council on Animal Care and were approved by the Institutional Animal Care and Use Committee (IACUC) at University of Oklahoma Health Sciences Center (OUHSC). Male Apc$^{Min/+}$ (C57BL/6J) and female wild-type littermate mice were initially purchased from The Jackson Laboratory (Bar Harbor, Me.) as founders, and our own breeding colony was established in OUHSC rodent barrier facility and genotyped according to vendor's instructions. All mice were housed 3 per cage in ventilated cages under standardized conditions (21° C., 60% relative humidity, 12 h light/12 h dark cycle, 20 air changes/hr). All mice were allowed ad libitum access to the respective diets and automated tap water purified by reverse osmosis.

Diets:

All diet ingredients for the semi-purified diets were purchased from Bioserve (Frenchtown, N.J.) and stored at 4° C. before diet preparation. Diets were based on the modified American Institute of Nutrition (AIN)-76A diet. LFA-9 was premixed with a small quantity of diet and then blended into bulk diet using a Hobart mixer. Both control and experimental diets were prepared weekly and stored in a cold room. Agent content in the experimental diets was determined periodically in multiple samples taken from the top, middle, and bottom portions of individual diet preparations to verify uniform distribution. In this study, we used 0 ppm, 350 ppm, 700 ppm LFA9 in the control diets.

Intestinal Tumorigenesis Studies in $Apc^{Min/+}$ Mice:

Genotyped Male and female $Apc^{Min/+}$ mice were used in the efficacy study. The experimental protocol is summarized in FIG. 2A. Five week old mice were distributed so that average body weights in each group were equal (10/9 $Apc^{Min/+}$ mice in each group) and were fed with AIN-76A diet for one week. At 6 weeks of age, mice were fed with control or experimental diets containing 0 ppm, 350 ppm, or 700 ppm LFA9 in the diet until termination of the study. Body weight, food, and fluid consumption were monitored weekly for signs of weight loss or lethargy that might indicate intestinal obstruction or anemia. Mice were routinely checked for any abnormalities. After 12 weeks, all mice were euthanized by $CO_2$ asphyxiation, blood was collected immediately by heart puncture, and serum was separated by centrifugation and stored at −80° C. until further analysis. This point in time was chosen to minimize the risk of intercurrent mortality caused by severe progressive anemia, rectal prolapse, or intestinal obstruction, which usually occurs among Min mice at >20 weeks of age. After necropsy, the entire intestinal tract was harvested, flushed with 0.9% NaCl and opened longitudinally from the esophagus to the distal rectum. The tissue was flattened on filter paper to expose the tumors and briefly frozen on dry ice to aid visual scoring of tumors. The number, location, and size of visible tumors in the entire intestine were determined under a dissection microscope (×5). All tumors were scored and subdivided by location (duodenal, jejunal and ileum and colon) and size (>2 mm, 1-2 or <1 mm in diameter). This procedure was completed by two individuals who were blinded to the experimental group and the genetic status of the mice. Colonic and other small intestinal tumors that required further histopathologic evaluation to identify adenoma, adenocarcinoma, and enlarged lymph nodes were fixed in 10% neutral-buffered formalin, embedded in paraffin blocks, and processed by routine H&E staining. In addition, multiple samples of tumors from the small intestines were harvested and stored in liquid nitrogen for analysis of molecular markers activities and expression levels.

Statistical Analyses:

All results are expressed as mean±SE and were analyzed by Student's t test. Differences were considered significant at the P<0.05 level. All statistical analysis was performed using GraphPad Prism Software 5.1 (GraphPad Software, Inc, San Diego, Calif.).

Figure 2:
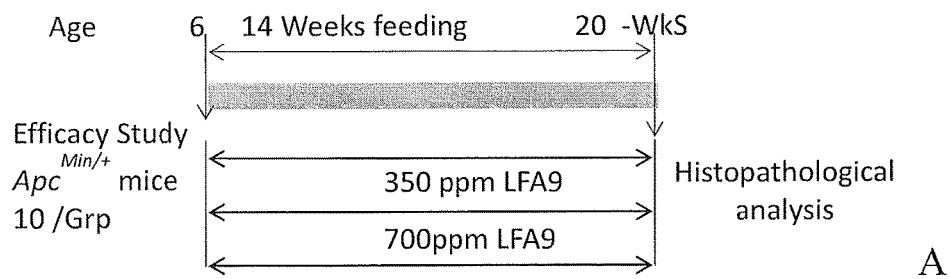
FIG. 2 is a graphical representation of (a) the experimental design used in the experimental analyses described herein, (b) body weights of male mice over time after treatment with LFA-9, and (c) body weights of female mice over time after treatment with LFA-9.
Figure 2:
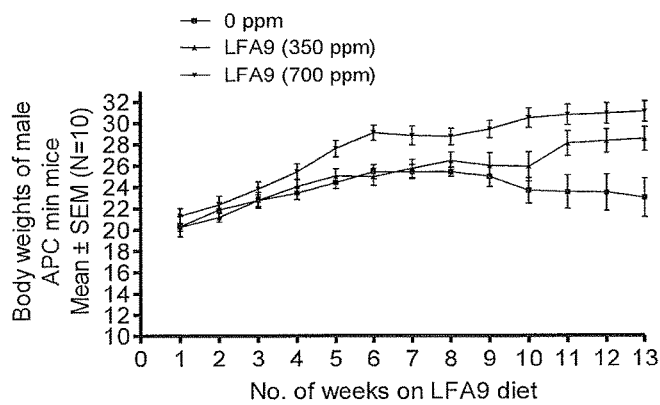
Figure 2:
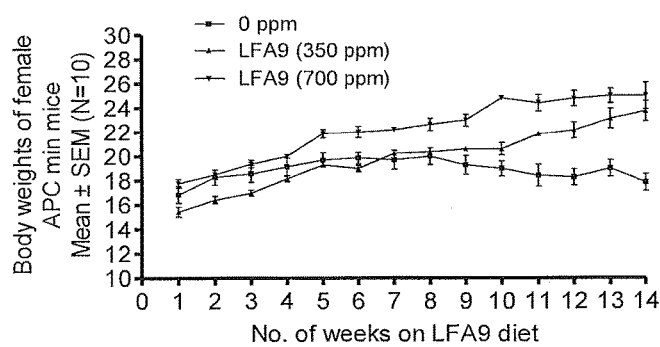

Health Monitoring of Mice:

Body weights of the $Apc^{Min/+}$ mice that consumed LFA-9 in their diets were, in general, higher weight gains and the mice were less anemic than those fed a control diet. Statistically significant (P>0.05) differences in body weights were observed between the dietary groups (FIGS. 2B and C). $Apc^{Min/+}$ mice spontaneously develop intestinal tumors, mostly in the small intestine with fewer tumors in the colon. As expected, control $Apc^{Min/+}$ mice began to lose body weight at ~14 weeks of age, due to intestinal obstruction and progressive anemia. In wild-type mice, the administration of LFA9 did not produce any gross changes attributable to toxicity in liver, kidneys or lungs and also had no effect on body weight gain.

Figure 3:
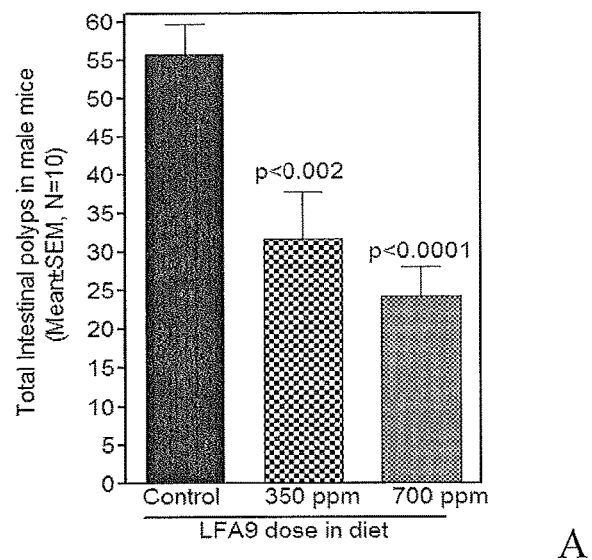
FIG. 3 shows the total number, and size of small intestinal tumors (polyps) in $Apc^{Min/+}$ male mice (A and B, respectively) after treatment with LFA-9.
Figure 3:
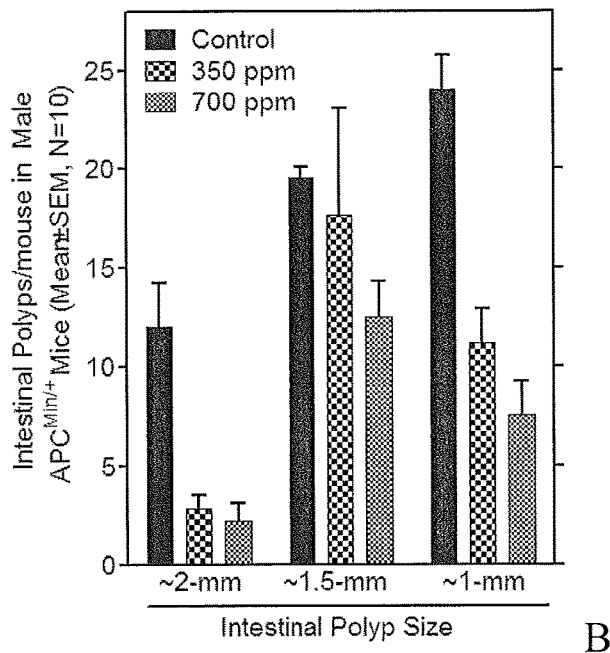
Figure 4:
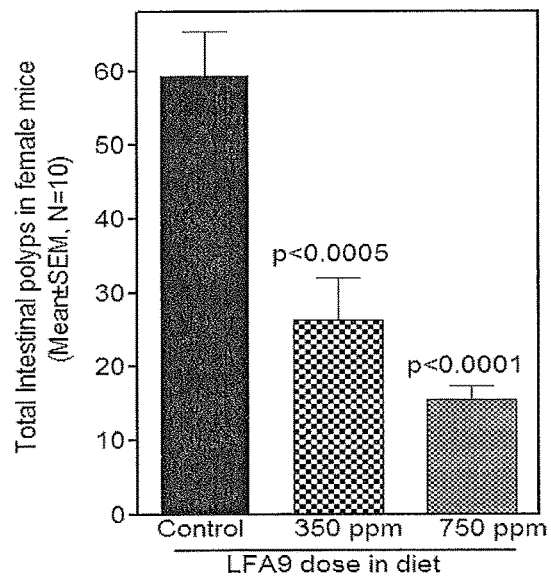
FIG. 4 shows the total number, and size of small intestinal tumors (polyps) in $Apc^{Min/+}$ female mice (A and B, respectively) after treatment with LFA-9.
Figure 4:
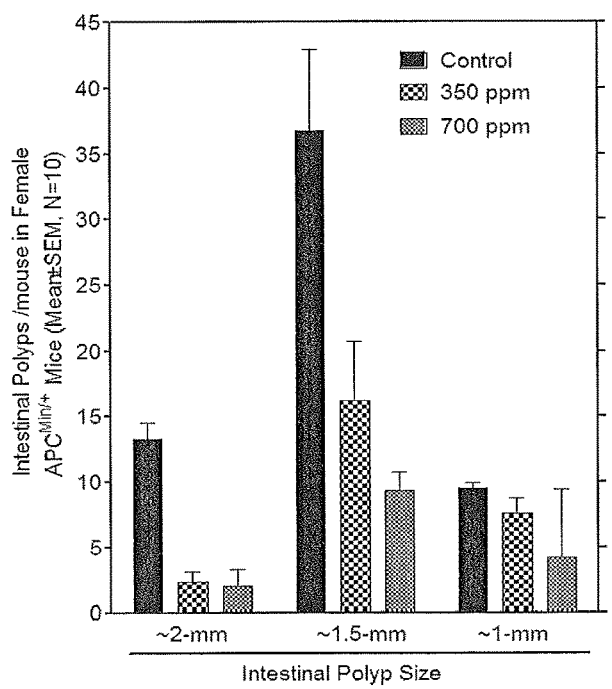
Figure 5:
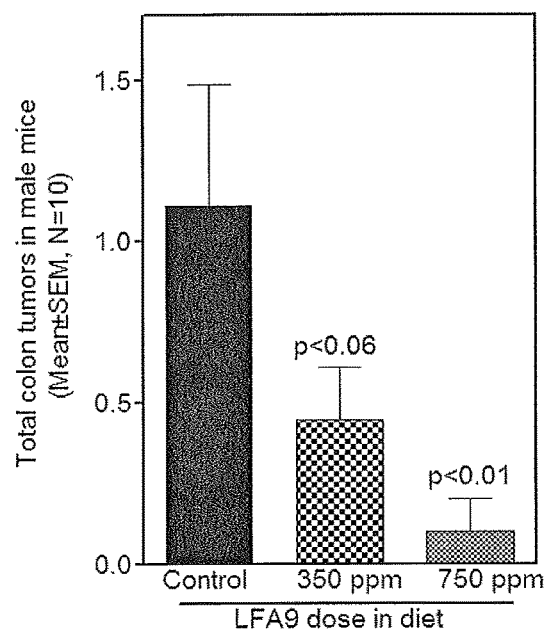
FIG. 5 shows the total number of colon tumors in $Apc^{Min/+}$ male mice (A) and in $Apc^{Min/+}$ female mice (B), after treatment with LFA-9.
Figure 5:
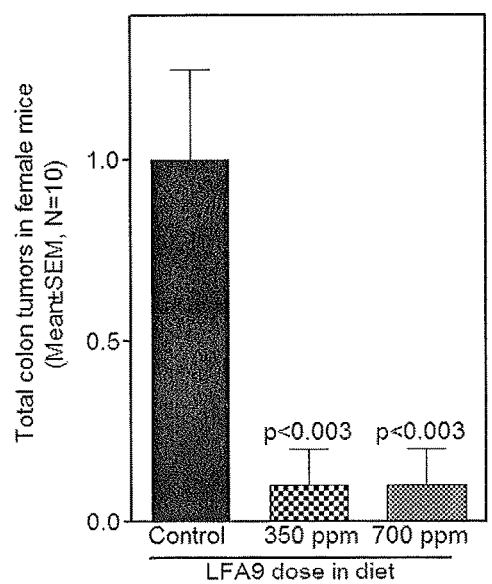

(B) Efficacy Results of $Apc^{Min/+}$ Mice Fed 350 and 700 ppm LFA-9:

LFA-9 prevents the development of polyps in Apc mutant transgenic mice. For these experiments, we examined the colon tumors and polyps of different size and number in different regions of the small intestine in these mice. Male and female $Apc^{Min/+}$ mice fed with control diet developed an average of 55.7±3.83 and 59.2±5.98 intestinal polyps, respectively (FIG. 3A, FIG. 4A). LFA9 administration at 350 and 700 ppm for 14 weeks significantly reduced total intestinal tumor multiplicity and size dose dependently in both male and female mice (means±SEM tumors for 350 and 700 ppm; 31.6±5.99 and 24.3±3.7, respectively, in male mice; and 26.2 5.68 and 15.5±1.79, respectively, in female mice; FIG. 3A, FIG. 4A). High-dose LFA9 showed approximately 56% (P<0.0001) and 73.8% intestinal tumor inhibition in male and female mice respectively. Interestingly, the number of large-sized polyps (>2 mm) was dramatically reduced with LFA9 treatments (FIG. 3B, FIG. 4B). Mice fed with 350 ppm LFA9 had 76.8% (male) and 81.6% (female) fewer polyps with sizes greater than 2 mm. Mice fed 700 ppm LFA9 showed more than 81% suppression of polyps of greater than 2 mm size in both genders compared with control mice (FIG. 3B, FIG. 4B). The mean number of colon tumors in male and female mice was 1.11 and 1.0, respectively, in control diet-fed mice; whereas mice fed with 350 ppm LFA9 showed colon tumor inhibition of 60% (male) and 90% (female), respectively. It is noteworthy that both male and female mice fed with 700 ppm LFA9 showed 91% inhibition of colon tumors (FIG. 5A,B). Female mice treated with LFA9 (350 and 700 ppm; 9/10 per treatment group) had a 90% reduction in the colonic tumors (1.22-0.1 tumors per mouse, P<0.003) compared to control untreated mice (FIG. 5B).

(C) I. Efficacy of LFA-9 in AOM-Induced Rat Colon Adenocarcinoma (AC) Formation

Rat-AOM Tumor Efficacy Studies:

LFA-9 at doses 200, 400 and 800 ppm has been evaluated by administering at late ACF/early adenomas stage of AOM-induced colon carcinogenesis, i.e., 7 weeks after carcinogen treatment. During the course of bioassay, we have assessed the effect of doses of LFA-9 on bodyweight gain. Chronic administration of LFA-9 up to 800 ppm in the diet did not show any significant body weight retardation and any observable toxicities.

After 42 weeks of experimental diet feeding and total 52 weeks of experimental duration, the rats were necropsied. After necropsy of the rats, the colonic tumors were analyzed histologically. Histopathological evaluation colonic tumor has been completed by two pathologists independently. Colonic tumors were histopathologically classified to adenomas or adenocarcinomas either exophytic (non-invasive) or endophytic (invasive). Based on the gross histological observations LFA-9 significantly suppressed AOM-induced colonic tumors. Colon tumor incidences (% of rats with colonic tumors) are summarized Table 2 and tumor multiplicity (mean colonic tumors/rat) in Table 5. Based on the histopathology, we observed about 34% of colonic tumors were adenomas and remaining 66% adenocarcinomas with majority (69%) non-invasive and fewer (31%) invasive. As shown in Tables 4 and 5, administration of LFA-9 in the diet suppressed both colonic adenomas incidence (53 to 48%) and multiplicity (38 to 47%). Moreover, dietary LFA-9 showed suppression of incidence and multiplicity of both non-invasive and invasive adenocarcinoma inhibition (>63% to 92%). Overall, mPGES-1 inhibitor LFA-9 significantly suppressed progression of early adenomas to adenocarcinoma formation in an extensive manner.

Figure 6:
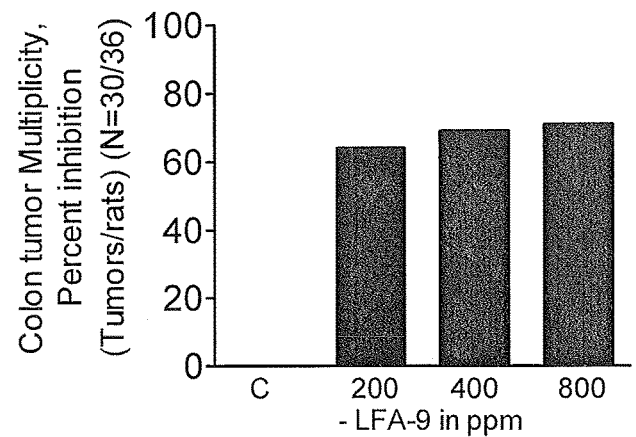
FIG. 6 shows the inhibitory effect of LFA-9 treatment on colon tumor multiplicity in F344 rats.

Results:
The effects of dietary administration of LFA-9 on azoxymethane-induced colon tumorigenesis were evaluated. LFA-9 treatment, at all the doses, significantly decreased total colon tumor multiplicity: at 200 ppm to 64%, at 400 ppm to 69.1%, and at 800 ppm to 71.1%, $p<0.0001$ (FIG. 6). Colonic tumors were histopathologically divided into

TABLE 4

Effect of LFA-9 on AOM-Induced Colon Tumor Incidence (Percentage rats with tumors) in male F344 rats.

| No | Experimental Groups | No of Rats | dose | Adenoma Incidence b (% Rats with Adenomas) | % adenoma Inhibition | Non-Inv AdCa Incidence (% Rats with Non-Inv AdCa) | % Non-Inv AdCA Inhibition | Invasive AdCA Incidence (% Rats with Invasive AdCA) |
|---|---|---|---|---|---|---|---|---|
| | AOM-Treated | | | | | | | |
| 1 | Control diet | 36 | 0 ppm | 23/36[a] (63.9%) | — | 26/36 (72.2%) | — | 16/36 (44.4%) |
| 2 | LFA-9 | 30 | 200 ppm | 9/30 (30.0%) | 53.0% $P < 0.0074$ | 8/30 (26.7%) | 63.0% $P < 0.0004$ | 2/30 (6.66%) |
| 3 | LFA-9 | 30 | 400 ppm | 9/30 (30.0%) | 53.0% $P < 0.0074$ | 6/30 (20.0%) | 72.3% $P < 0.0001$ | 3/30 (10.0%) |
| 4 | LFA-9 | 30 | 800 ppm | 8/30 (26.7%) | 58.2% $P < 0.0032$ | 6/30 (20.0%) | 72.3% $P < 0.0001$ | 1/30 (3.33%) |
| | Saline Treated | | | | | | | |
| 5 | Control Diet | 12 | 0 ppm | 0 | — | 0 | — | 0 |
| 6 | LFA-9 | 12 | 800 ppm | 0 | — | 0 | — | 0 |

| No | Experimental Groups | % Inv AdCA Inhibition | AdCA Incidence (% Rats with AdCa) | % AdCA Inhibition | Total CRC Tumors (Adenoma + AdCa) | % of CRC Tumor Inhibition |
|---|---|---|---|---|---|---|
| | AOM-Treated | | | | | |
| 1 | Control diet | — | 30/36 (83.3%) | — | 32/36 (88.9%) | — |
| 2 | LFA-9 | 85.1% $P < 0.0001$ | 10/30 (33.3%) | 60.0% $P < 0.0001$ | 14/30 (46.6%) | 47.5% $P < 0.0003$ |
| 3 | LFA-9 | 77.4%% $P < 0.0003$ | 8/30 (26.7%) | 67.9% $P < 0.0001$ | 12/30 (40.0%) | 55.0% $P < 0.0001$ |
| 4 | LFA-9 | 92.5% $P < 0.0001$ | 6/30 (20.0%) | 76.0% $P < 0.0001$ | 14/30 (46.6%) | 47.5% $P < 0.0001$ |
| | Saline Treated | | | | | |
| 5 | Control Diet | — | 0 | — | 0 | — |
| 6 | LFA-9 | — | 0 | — | 0 | — |

Figure 7:
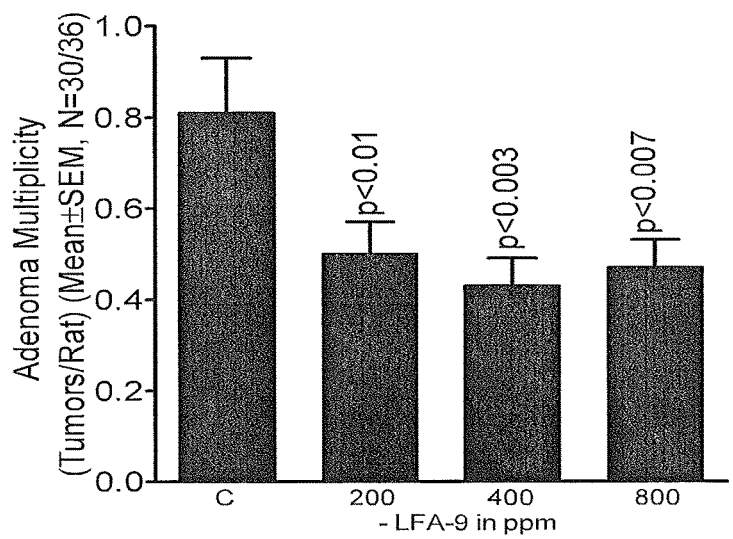
FIG. 7 shows the effect of LFA-9 treatment on adenoma multiplicity in F344 rats.
Figure 8:
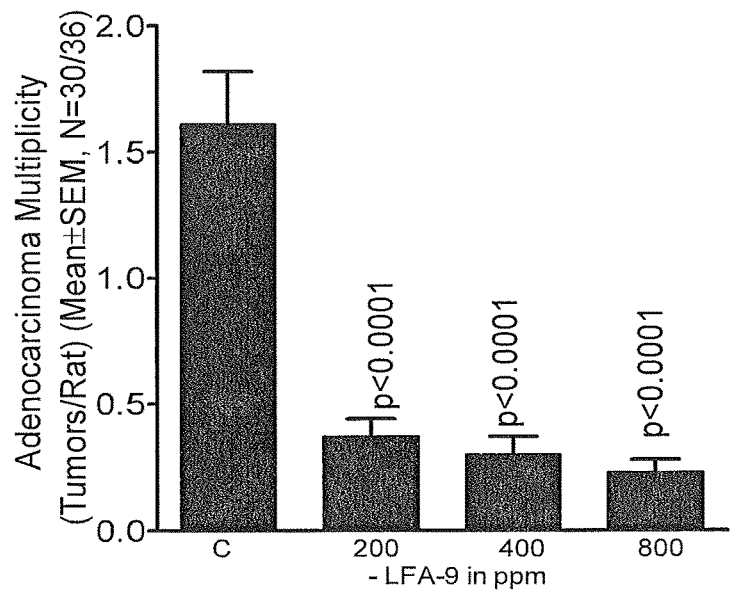
FIG. 8 shows the effect of LFA-9 treatment on adenocarcinoma multiplicity in F344 rats.
Figure 9:
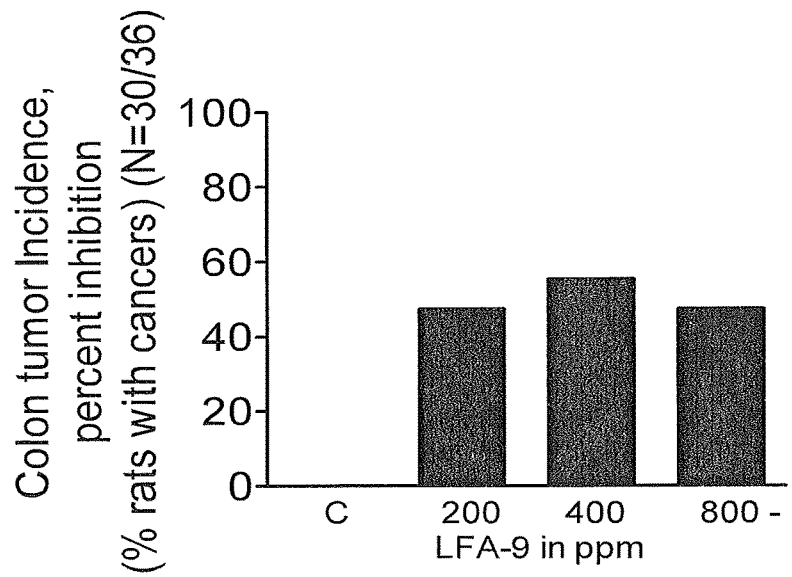
FIG. 9 shows the inhibitory effect of LFA-9 treatment on colon tumor incidence in F344 rats.
Figure 10:
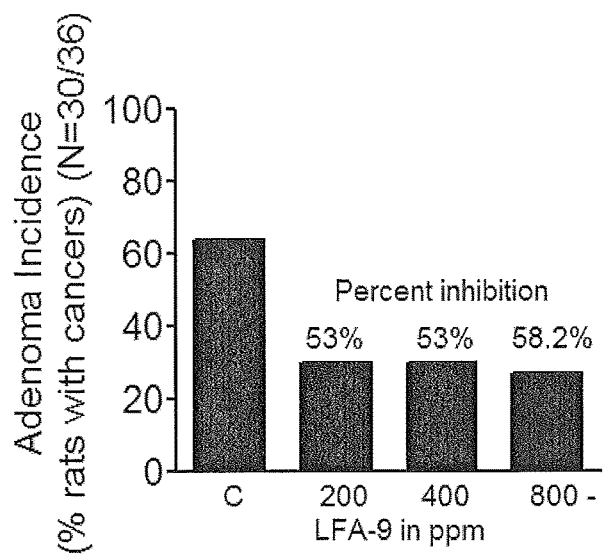
FIG. 10 shows the inhibitory effect of LFA-9 treatment on adenoma incidence in F344 rats.
Figure 11:
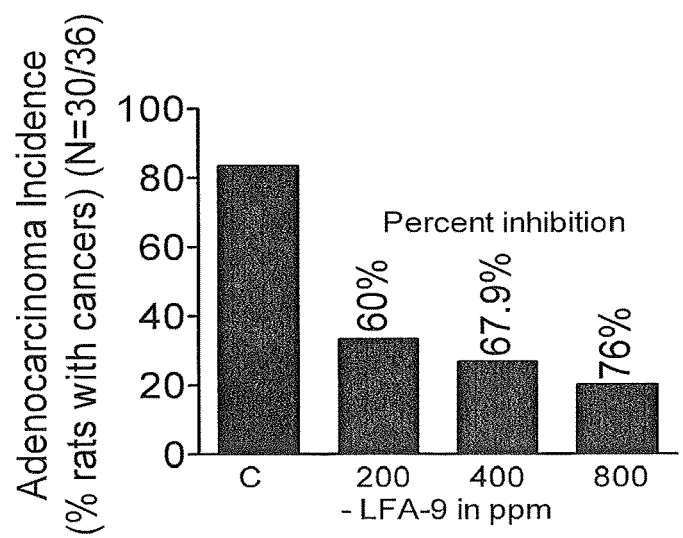
FIG. 11 shows the inhibitory effect of LFA-9 on adenocarcinoma incidence in F344 rats.

[a] Values are from rats with percentage of colonic tumors; N = 36 animals in control group and N = 30, in treatment groups
b adenomas or Adenocarcinomas incidence (% of rats with colonic tumors).
[c] Significantly different from Control diet fed group, by Fisher's Exact two tail test (C) II. Inhibitory Effect of LFA-9 on Azoxymethane-Induced Colon Adenoma and Adenocarcinoma Incidence in Male F344 Rats Biological Assay:

Colonic tumors (CTs) were induced by colon specific carcinogen, azoxymethane (AOM) (15 mg/kg by wt, once weekly for 2 weeks) in F344 rats at 8 weeks' age. Rats were maintained on AIN-76A diet or AIN-76A diet containing 200 ppm, 400 ppm or 800 ppm of LFA-9 for 32 weeks. Rats were killed by $CO_2$ asphyxiation 36 weeks after second AOM and the colons were removed, rinsed in PBS, opened longitudinally, and flattened on a filter paper. The location and size of each tumor were noted. Tumors were removed, snap frozen, or fixed in 10% buffered formalin for 24 hours and transferred to 80% ethanol for histopathological analysis. The number and type of colon tumors (adenoma and adenocarcinoma) were analyzed histologically blinded to treatment groups and compared with control diet fed rat colonic tumors.

adenoma (non-malignant) and adenocarcinomas (malignant). A significant reduction in adenoma multiplicity was observed with all the doses of LFA-9 tested: 200 ppm, 38.3%, (0.50±0.07, P<0.015); 400 ppm, 46.9%, (0.43±0.06, P<0.0033) and high dose 800 ppm, 42%, (0.47±0.06, P<0.0072), as shown in FIG. 7, when compared with control diet group. Importantly, LFA-9 caused a significant reduction in adenocarcinoma multiplicity at 200 ppm to 77% inhibition (0.37±0.07, P<0.0001), at 400 ppm to 81.3% inhibition (0.30±0.07, p<0.0001) and at 800 ppm to 85.7% inhibition (0.23±0.05, p<0.0001) as compared with control diet fed rat colonic adenocarcinomas (FIG. 8). LFA-9 showed a significant effect on the incidence (percentage of rats with colonic tumors) of colon tumors compared with control diet fed rats by 47.5% at 200 ppm, 55.5% at 400 ppm and 47.5% at 800 ppm (FIG. 9). Similarly, LFA-9 at 200 ppm, 400 ppm and 800 ppm caused a significant reduction in colon adenoma incidence (53%, 53%, and 58.2%; FIG. 10). Importantly, LFA-9 showed to be much more protective by inhibiting AOM-induced colon adenocarcinoma incidence (60%, 67.9% and 76%; FIG. 11) as compared with control diet group rat colon adenocarcinoma incidence. It is noteworthy that even low doses of LFA-9 showed a significant effect on the incidence of adenoma and adenocarcinomas. Overall, LFA-9 caused significant reduction in the colon tumor incidence and multiplicity compared with control diet group.

(D) Effect of mPGES-1 Inhibitors on AOM-Induced Colon Tumor Incidence:

As shown in the Table 4 tumor incidence were presented in the form of adenoma, adenocarcinoma of non-invasive or invasive or total adenocarcinomas and total colorectal tumor incidence. Rats exposed to AOM-treatment showed 64% rats with adenomas (mostly tubular and very few villous) and 83% rats with adenocarcinomas with majority non-invasive type at the time of termination. Also, histopathology of tumors suggests about 44% rats with highly invasive colonic adenocarcinomas in carcinogen treated and control diet fed rats. Administration of LFA-9 in the diet significantly suppressed colonic adenomas incidence (53 to 58%). Moreover, dietary LFA-9 showed suppression of incidence of both non-invasive and invasive adenocarcinoma inhibition (63% to 92%). Overall, both mPGES-1 inhibitors significantly suppressed colon tumor incidence by inhibiting and delaying progression of early adenomas to adenocarcinoma formation in an extensive manner.

(E) Effect of mPGES-1 Inhibitors on AOM-Induced Colon Tumor Multiplicity:

Table 5 displays the colon tumor multiplicities (mean colonic tumors per rat) induced with a colon carcinogen in rats fed control diet or mPGES-1 inhibitors. Tumor multiplicities were presented in the form of adenoma, adenocarcinoma of non-invasive or invasive or total adenocarcinomas and with overall colorectal tumor multiplicities. Rats fed control diet had $1.11\pm0.15$ non-invasive and $0.50\pm0.08$ invasive adenocarcinomas. Administration of LFA-9 in the diet significantly suppressed colonic adenomas multiplicity (38 to 47%). Also, dietary LFA-9 showed suppression of both non-invasive and invasive adenocarcinoma multiplicity (77% to 94%). Overall, mPGES-1 inhibitor LFA-9 significantly suppressed colon tumor multiplicities by inhibiting and delaying progression of early adenomas to adenocarcinoma formation in an extensive manner.

TABLE 5

Effect of LFA-9 on AOM-Induced Colon Tumor Multiplicity (Mean Tumors/Rat) in male F344 rats.

| | | No of Rats | No | Experimental Groups | % adenoma Inhibition | Non-Inv AdCa Multiplicity (% Rats with Non-Inv AdCa) | % Non-Inv AdCA Inhibition |
|---|---|---|---|---|---|---|---|
| AOM-Treated | | | | | | | |
| 1 | Control diet | 36[c] | 0 ppm | $0.81 \pm 0.12$ | — | $1.11 \pm 0.15$ | — |
| 2 | LFA-9 | 30 | 200 ppm | $0.50 \pm 0.07$ $p < 0.015$ | 38.27% | $0.30 \pm 0.05$ $p < 0.0001$ | 72.9% |
| 3 | LFA-9 | 30 | 400 ppm | $0.43 \pm 0.06$ $p < 0.0033$ | 46.9% | $0.20 \pm 0.04$ $p < 0.0001$ | 82.0% |
| 4 | LFA-9 | 30 | 800 ppm | $0.47 \pm 0.06$ $p < 0.0072$ | 42.0% | $0.20 \pm 0.04$ $p < 0.0001$ | 82.0% |
| Saline Treated | | | | | | | |
| 5 | Control Diet | 12 | 0 ppm | 0 | — | 0 | — |
| 6 | LFA-9 | 12 | 800 ppm | 0 | — | 0 | — |

| | | Invasive AdCA Multiplicity (% Rats with Invasive AdCa) | % Inv AdCA Inhibition | AdCA Multiplicity (% Rats with AdCa) | % AdCA Inhibition | Multiplicity Total CRC Tumors (Adenoma + AdCa) | % of CRC Tumor Inhibition |
|---|---|---|---|---|---|---|---|
| AOM-Treated | | | | | | | |
| 1 | Control diet | $0.50 \pm 0.08$ | — | $1.61 \pm 0.21$ | — | $2.42 \pm 0.28$ | — |
| 2 | LFA-9 | $0.07 \pm 0.02$ $p < 0.0001$ | 86.0% | $0.37 \pm 0.07$ $p < 0.0001$ | 77.0% | $0.87 \pm 0.12$ $p < 0.0001$ | 64.05% |
| 3 | LFA-9 | $0.10 \pm 0.02$ $p < 0.0001$ | 80.0% | $0.30 \pm 0.07$ $p < 0.0001$ | 81.3% | $0.73 \pm 0.10$ $p < 0.0001$ | 69.08% |
| 4 | LFA-9 | $0.03 \pm 0.01$ $p < 0.0001$ | 94.0% | $0.23 \pm 0.05$ $p < 0.0001$ | 85.7% | $0.70 \pm 0.10$ $p < 0.0001$ | 71.07% |
| Saline Treated | | | | | | | |
| 5 | Control Diet | 0 | — | 0 | — | 0 | — |
| 6 | LFA-9 | 0 | — | 0 | — | 0 | — |

[a] Adenomas or Adenocarcinomas Multiplicity (Mean Colonic tumors/Rat).
[b] Significantly different from Control diet fed group, by "t"-test (one tail test) with Welch's correction).
[c] Values are Mean ± SEM, N = 36 animals in control group and N = 30, in treatment groups (F) Anti-Inflammatory Effects of LFA-9 in AOM-Induced Rat Colonic Tumors Biological Assay:

Colonic tumors (CTs) were induced by colon specific carcinogen Azoxymethane (15 mg/kg by wt, once weekly for 2 weeks) in F344 rats at 8 weeks' age. Rats were fed different doses of LFA-9 for 32 weeks. Rats were killed 36 weeks after second AOM and analyzed for inflammatory cytokines and receptors and compared with control diet fed rat colonic tumors.

Figure 12:
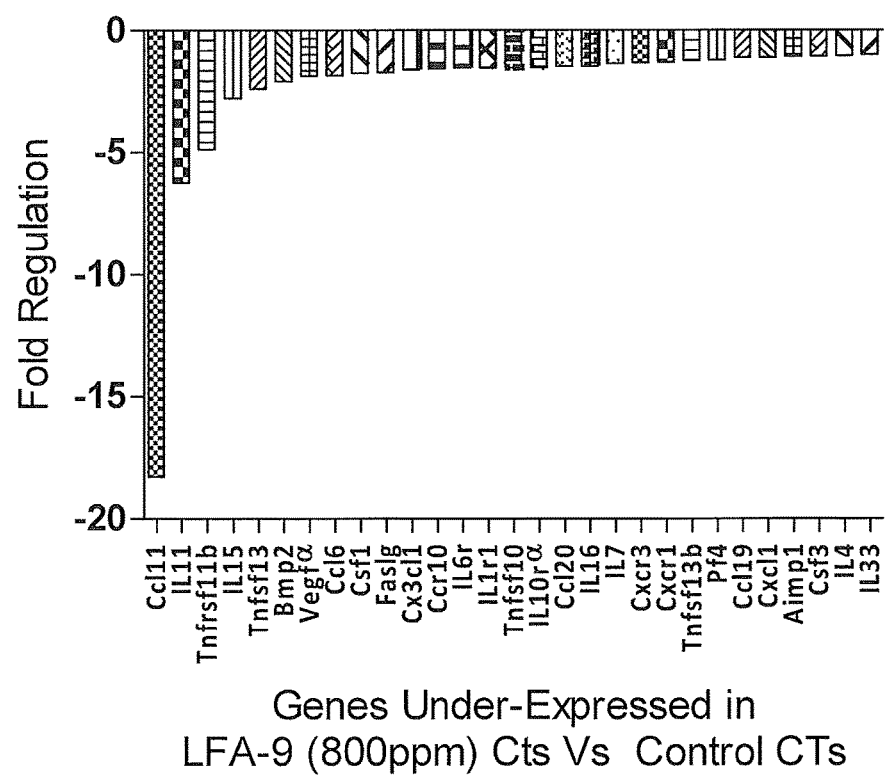
FIG. 12 shows the inhibitory effect of LFA-9 on inflammatory cytokines and receptors in colon tumors.

Inflammatory Cytokines and Receptors Real Time PCR Analysis:

Colon tumors from control diet fed rats and LFA-9 treated (800 ppm) animals were analyzed using inflammatory cytokines, receptors and genes PCR array involved in inflammatory responses from Qiagen. LFA-9 significantly altered genes upon treatment when compared to control colon tumors (FIG. 12). The results indicate that a number of inflammatory cytokines and their receptors significantly decreased and also several genes involved in Treg migration, EMT and metastases were reduced. Therefore, LFA-9 poses anti-inflammatory properties and decreased Ccl11, IL11, Tnfrsf11b, IL15, Tnfsf13, Bmp2, Vegfa, Ccl6, Csf1, Faslg, Cx3cl1, Ccr10, IL6, IL1r1, Tnfsf10, IL10ra, Ccl20, IL16, IL7, Cxcr1, Tnfsf13b, Pf4, Ccl19, Cxcl1, Aimp1, Csf3, IL4, IL33 in treated colon tumors.

Discussion

Minimum Toxic Dose:

Dietary LFA-9 administered to mice up to 800 ppm in the diet does not induce any toxicity and gained bodyweights similar to control diet fed mice. However, dietary LFA-9 administration at 1,600 ppm caused significant body weight retardation with notable stomach and colon ulceration, with an increase in liver enzymes and also 3 animals died as compared to control diet-fed mice. Overall, bodyweight and gross histological observations suggest that 800 ppm LFA-9 administered in the diet do not induce any body weight loss or gross histological symptoms of toxicity in C57BL/6 mice. LFA-9 doses up to 800 ppm tested showed no ulceration and proved to be anti-inflammatory in function as per the results of ulceration and inflammation scoring.

ACF Studies in Rat AOM-DSS Model:

AOM-DSS treatment significantly induced colonic inflammation and ACF formation. LFA-9 treatment at >100 ppm significantly suppressed infiltration of inflammatory cells in colonic mucosa and submucosa. LFA-9 (doses 200, 400, and 600 ppm) suppressed both total colonic ACF and multi-crypt ACs in a dose dependent manner.

Apc Min Mouse Study:

The results indicate that LFA-9 possesses effective chemopreventive properties in Apc$^{Min/+}$ mice without evidence of toxicity. LFA-9 showed dose dependent inhibition of small intestinal polyp's incidence and size in both the genders of Apc$^{Min/+}$ mice. Colon tumors were significantly reduced in both male and female Apc$^{Min/+}$ mice by both doses of LFA9. The doses used in this study were observed to be non-toxic as per the gross observation of the organs and the body weight gain by the experimental mice.

Rat AOM-Induced Colon Tumors:

Long term efficacy study results indicate that LFA-9 effectively inhibits AOM-induced colon tumors in rats. The doses tested in this study were observed to be non-toxic without any body weight loss and devoid of any organ toxicity in experimental rats. LFA-9 showed dose dependent inhibition of colon adenocarcinomas. It showed significant inhibition of both non-invasive and invasive colon adenocarcinoma multiplicities.

Overall, these studies indicate that LFA-9 significantly suppressed inflammation, mPGES-1, 5-LOX enzyme activities, intestinal tumors in Apc min mice, ACFs in AOM-DSS rat model and colon tumor incidence and multiplicity in AOM-induced rat model by inhibiting and delaying progression of early adenomas to adenocarcinoma formation significantly compared to control untreated animals.

Licofelone Derivatives

In certain non-limiting embodiments, the present disclosure includes compounds having the structural formula (Structure 1):

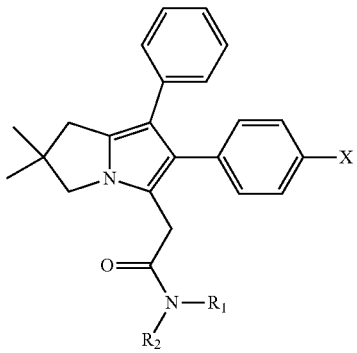

wherein X is selected from the group consisting of F, Cl, Br, and I; and $R_1$ and $R_2$ are selected from the group consisting of: H, $CH_2(CH_2)_n OH$, $CH_2(CH_2)_m COOH$, $CH((CH_2)_m CH_3)COOH$, $CH((CH_2)_n OH))COOH$, $CH((CH_2)_n COOH)COOH$, $CH_2(CH_2)_n NH_2$, $CH((CH_2)_n CONH_2)COOH$, $CH((CH_2)_n NH_2)COOH$, $CH((CH_2)_n NHC(NH)NH_2)COOH$, and $CH_2(CH_2)_n F$, wherein m=0-3 and n=1-3; and with the proviso that no more than one of $R_1$ and $R_2$ is H.

For example, in certain non-limiting embodiments, $R_1$ and $R_2$ may be selected from the group consisting of H; $CH_2CH_2OH$; $CH_2(CH_2)_2OH$; $CH_2(CH_2)_3OH$; $CH_2COOH$; $CH_2CH_2COOH$; $CH_2(CH_2)_2COOH$; $CH_2(CH_2)_3COOH$; $CH(CH_3)COOH$; $CH(CH_2CH_3)COOH$; $CH((CH_2)_2CH_3)COOH$; $CH((CH_2)_3CH_3)COOH$; $CH(CH_2OH))COOH$; $CH((CH_2)_2OH))COOH$; $CH((CH_2)_3OH))COOH$; $CH(CH_2COOH)COOH$; $CH((CH_2)_2COOH)COOH$; $CH((CH_2)_3COOH)COOH$; $CH_2CH_2NH_2$; $CH_2(CH_2)_2NH_2$; $CH_2(CH_2)_3NH_2$; $CH(CH_2CONH_2)COOH$; $CH((CH_2)_2CONH_2)COOH$; $CH((CH_2)_3CONH_2)COOH$; $CH(CH_2NH_2)COOH$; $CH((CH_2)_2NH_2)COOH$; $CH((CH_2)_3NH_2)COOH$; $CH(CH_2NHC(NH)NH_2)COOH$; $CH((CH_2)_2NHC(NH)NH_2)COOH$; $CH((CH_2)_3NHC(NH)NH_2)COOH$; $CH_2CH_2F$; $CH_2(CH_2)_2F$; and $CH_2(CH_2)_3F$; wherein no more than one of $R_1$ and $R_2$ is H. In one non-limiting embodiment, the licofelone derivative is LFA-9 (i.e., licofelone-glycine), wherein X=Cl, one of $R_1$ and $R_2$=H, and one of $R_1$ and $R_2$=$CH_2COOH$.

The compound(s) may be disposed in a pharmaceutically-acceptable carrier, diluent, or vehicle to form a composition. The compound(s) or composition(s) containing the compound(s) may be used in a method of treating an inflammatory-related disease or condition in a subject in need of such therapy, for example wherein the inflammatory-related disease or condition is atherosclerosis, diabetes, inflammatory bowel diseases, arthritis, psoriasis, autoimmune diseases, Alzheimer's disease, or a cancer associated with a chronic inflammatory component, wherein the method comprises administering to the subject a therapeutically-effective amount of the compound or composition. Examples of cancers associated with a chronic inflammatory component include epithelial carcinoma cancers such as colorectal, pancreatic, lung, peritoneal, bladder, breast, prostate, renal, liver, bile duct, testicular, skin, stomach, ovarian, fallopian tube, and uterine cancers.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

What is claimed is:

1. A compound comprising the structural formula:

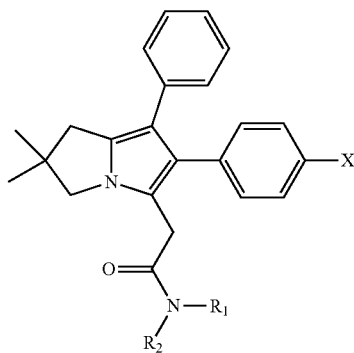

wherein
X is selected from the group consisting of F, Cl, Br, and I; and
R$_1$ and R$_2$ are selected from the group consisting of: H, CH$_2$(CH$_2$)$_n$OH, CH$_2$(CH$_2$)$_m$COOH, CH((CH$_2$)$_m$CH$_3$)COOH, CH((CH$_2$)$_n$OH))COOH, CH((CH$_2$)$_n$COOH)COOH, CH$_2$(CH$_2$)$_n$NH$_2$, CH((CH$_2$)$_n$CONH$_2$)COOH, CH((CH$_2$)$_n$NH$_2$)COOH, CH((CH$_2$)$_n$NHC(NH)NH$_2$)COOH, and CH$_2$(CH$_2$)$_n$F, wherein m=0-3 and n=1-3; and with the proviso that no more than one of R$_1$ and R$_2$ is H.

2. The compound of claim 1, wherein X=Cl, one of R$_1$ and R$_2$=H, and one of R$_1$ and R$_2$=CH$_2$COOH.

3. A composition comprising the compound of claim 1, and a pharmaceutically-acceptable carrier, diluent, or vehicle.

4. A method of treating an inflammatory-related disease or condition in a subject in need of such therapy, comprising:
administering to the subject an effective amount of a compound comprising the structural formula:

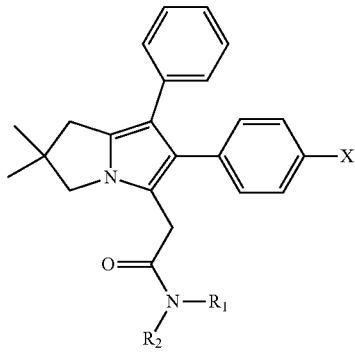

wherein
X is selected from the group consisting of F, Cl, Br, and I; and
R$_1$ and R$_2$ are selected from the group consisting of: H, CH$_2$(CH$_2$)$_n$OH, CH$_2$(CH$_2$)$_m$COOH, CH((CH$_2$)$_m$CH$_3$)COOH, CH((CH$_2$)$_n$OH))COOH, CH((CH$_2$)$_n$COOH)COOH, CH$_2$(CH$_2$)$_n$NH$_2$, CH((CH$_2$)$_n$CONH$_2$)COOH, CH((CH$_2$)$_n$NH$_2$)COOH, CH((CH$_2$)$_n$NHC(NH)NH$_2$)COOH, and CH$_2$(CH$_2$)$_n$F, wherein m=0-3 and n=1-3; and with the proviso that no more than one of R$_1$ and R$_2$ is H.

5. The method of claim 4, wherein in the compound X=Cl, one of R$_1$ and R$_2$=H, and one of R$_1$ and R$_2$=CH$_2$COOH.

6. The method of claim 4, wherein the compound is a component of a composition comprising a pharmaceutically-acceptable carrier, diluent, or vehicle.

7. The method of claim 4, wherein the inflammatory-related disease or condition is selected from the group consisting of atherosclerosis, diabetes, inflammatory bowel diseases, arthritis, psoriasis, autoimmune diseases, Alzheimer's disease, and a cancer associated with a chronic inflammatory component.

8. The method of claim 7, wherein the cancer associated with a chronic inflammatory component is an epithelial carcinoma cancer.

9. The method of claim 8, wherein the epithelial carcinoma cancer is selected from the group consisting of colorectal, pancreatic, lung, peritoneal, bladder, breast, prostate, renal, liver, bile duct, testicular, skin, stomach, ovarian, fallopian tube, and uterine cancers.

* * * * *